(12) United States Patent
Davis et al.

(10) Patent No.: US 9,057,092 B2
(45) Date of Patent: *Jun. 16, 2015

(54) METHODS AND COMPOSITIONS FOR IDENTIFYING A CELL PHENOTYPE

(71) Applicant: ZETIQ TECHNOLOGIES LTD., Tel Aviv (IL)

(72) Inventors: Noa Davis, Tel Aviv (IL); Adi Elkeles, Tel Aviv (IL); Dov Terkieltaub, Tel Aviv (IL); Alexander Chausovsky, Jerusalem (IL)

(73) Assignee: ZETIQ TECHNOLOGIES LTD., Tel Aviv (IL)

( * ) Notice: Subject to any disclaimer, the term of this patent is extended or adjusted under 35 U.S.C. 154(b) by 98 days.

This patent is subject to a terminal disclaimer.

(21) Appl. No.: 13/673,643

(22) Filed: Nov. 9, 2012

(65) Prior Publication Data

US 2013/0102025 A1    Apr. 25, 2013

Related U.S. Application Data

(63) Continuation-in-part of application No. 12/224,792, filed as application No. PCT/IL2007/000281 on Mar. 6, 2007, now Pat. No. 8,343,733.

(60) Provisional application No. 60/778,839, filed on Mar. 6, 2006, provisional application No. 60/778,944, filed on Mar. 6, 2006, provisional application No. 60/778,900, filed on Mar. 6, 2006, provisional application No. 60/778,902, filed on Mar. 6, 2006.

(51) Int. Cl.
| | | |
|---|---|---|
| C12Q 1/02 | (2006.01) | |
| C12N 5/06 | (2006.01) | |
| C12Q 1/04 | (2006.01) | |
| G01N 33/574 | (2006.01) | |

(52) U.S. Cl.
CPC ............ *C12Q 1/04* (2013.01); *G01N 33/57492* (2013.01)

(58) Field of Classification Search
CPC .......................... C12Q 1/04; G01N 33/57492
USPC ................................................ 435/6.14, 34
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman | |
| 4,034,074 A | 7/1977 | Miles | |
| 4,036,945 A | 7/1977 | Haber | |
| 4,098,876 A | 7/1978 | Piasio et al. | |
| 4,331,647 A | 5/1982 | Goldenberg | |
| 4,666,828 A | 5/1987 | Gusella | |
| 4,683,202 A | 7/1987 | Mullis | |
| 4,698,360 A | 10/1987 | Masquelier | |
| 4,801,531 A | 1/1989 | Frossard | |
| 4,879,219 A | 11/1989 | Wands | |
| 4,946,778 A | 8/1990 | Ladner | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 6,051,393 A | 4/2000 | Jones et al. | |
| 6,284,543 B1 | 9/2001 | Alvarez | |
| 8,012,678 B2 | 9/2011 | Pyeon et al. | |
| 2002/0058028 A1 | 5/2002 | Malmros et al. | |
| 2004/0260157 A1 | 12/2004 | Montes | |
| 2005/0181429 A1 | 8/2005 | Fejgin et al. | |
| 2009/0117610 A1 | 5/2009 | Gelvan et al. | |
| 2009/0221430 A1 | 9/2009 | Wu | |
| 2011/0318756 A1 | 12/2011 | Tsivis | |

FOREIGN PATENT DOCUMENTS

| | | |
|---|---|---|
| WO | 96/16334 A2 | 5/1996 |
| WO | 03/091729 A1 | 11/2003 |
| WO | 2004/086937 A2 | 10/2004 |
| WO | 2007/015926 A2 | 2/2007 |
| WO | 2007/102146 A2 | 9/2007 |
| WO | 2009/055052 A2 | 4/2009 |

OTHER PUBLICATIONS

Achilonu et al., (2008) Synthesis of Proanthocyanidins. Part 1. The First Oxidative Formation of the Interflavanyl Bond in Procyanidins. Organic Letters 10 (17): 3865-3868.

Anantaraman and Ravindranath (1976) Histochemical characteristics of the egg envelopes of Acanthosentis sp. (*Acanthocephala*). Z Parasitenkd 48: 227-38.

Dilek et al., (1998) Mucin production in carcinomas of the uterine cervix. Exp J Obstet Gynecol 79: 149-151.

Fukuda et al., (1980) Fluorescence fading and stabilization in cytofluorometry. Histochem 65: 269-276.

Klein et al., (2005) Transitional cell hyperplasia and carcinomas in urinary bladders of transgenic mice with keratin 5 promoter-driven cyclooxygenase-2 overexpression. Cancer Res 65: 1808-1813.

(Continued)

*Primary Examiner* — Tekchand Saidha
*Assistant Examiner* — Md. Younus Meah
(74) *Attorney, Agent, or Firm* — Rothwell, Figg, Ernst & Manbeck, P.C.

(57) ABSTRACT

The present invention is directed to a method of identifying cancerous or precancerous cells suspended in a liquid carrier, such as, a biological fluid.

20 Claims, 2 Drawing Sheets

(56) References Cited

OTHER PUBLICATIONS

Nifli et al., (2005) Monomeric and oligomeric flavanols are agonists of membrane androgen receptors. Exp Cell Res 309: 329-339.

Shao et al., (2003) Grape seed proanthocyanidin extract attenuates oxidant injury in cardiomyocytes. Pharmacological Research 47: 463-469.

Zhang et al., (2005) Proanthocyanidin from grape seeds potentiates anti-tumor activity of doxorubicin via immunomodulatory mechanism. Int Immunopharmacol 5: 1247-1257.

Desmedt, Christine et al., (2009) Quantitation of HER2 expression or HER2:HER2 dimers and differential survival in a cohort of metastatic breast cancer patients carefully selected for trastuzumab treatment primarily by FISH. Diag Mol Pathol 18(1):22-29 Abstract.

Idelevich, Pavel et al., (2009) Novel Histochemical Stain for Tinctorial Detection of Cancer and Neoplastic Cells. The Journal of Histotechnology 32(3):97-105.

Komen, Job et al., (2008) Viability analysis and apoptosis induction of breast cancer cells in a microfluidic device: effect of cytostatic drugs. Biomed Microdevices 10(5):727-737.

Kortekangas-Savolainen, O. et al., (2006) Allergens of *Ficus benjamina* (weeping fig):Unique allergens in sap. Allergy 61(3)393-394.

Molnar, P. and Mehes, G. (2009) Predictive molecular pathological testing in the diagnosis of high-grade tumors of glial origin. Magyer Oncologia 53(1):33-38 article in Hungarian Abstract Only.

Steven, F. S. et al., (1996) Fluorescent location of cells of cytological interest in cervical smears prestained with thionin. Anticancer Res 16(3A):1193-1196.

Ye, X. et al., (1999) The cytotoxic effects of a novel IH636 grape seed proanthocyanidin extract on cultured human cancer cells. Mol Cell Biochem 196(1-2):99-108.

Database Biosis [online] Bioscience Information Service, Philadelphia, PA, US; 1986, Sackeyfio, A. C. et al: "The anti-inflammatory effect of a crude aqueous extract of the root bark of *Ficus-elastica* in the rat" Database accession No. PREV198682095850 abstract & Archives Internationales de Pharmacodynamie et de Therapie 281(1)169-176 1986.

"Staining" Wikipedia, the free incyclopedia retrieved from http://en.wikipedia.org/wiki/staining Nov. 8, 2010 (9 pages).

IPRP of PCT/IL2007/000281 dated Sep. 18, 2008.

ISR of PCT/IL2007/000281 dated Oct. 18, 2007.

IL 193805 Office action dated Nov. 7, 2010 and its translation into English and response to OA dated Mar. 27, 2011.

IL 211963 Office action dated Aug. 7, 2011 and its translation into English.

SG 200806458-6 Search Report and Written Opinion conducted by the Austrian Patent office dated Nov. 11, 2010 and response dated Mar. 24, 2011.

Duesbery et al., (2001) Suppression of ras-mediated transformation and inhibition of tumor growth and angiogenesis by anthrax lethal factor, a proteolytic inhibitor of multiple MEK pathways. Proc Natl Acad Sci U S A 98(7): 4089-4094.

Hamburger and Hamilton (1951) A series of normal stages in the development of the chick embryo. J Morphol 88(1): 49-92.

Papanicolaou and Traut (1941) The diagnostic value of vaginal smears in carcinoma of the uterus. Am J Obstet Gynecol 42(2): 193-206.

Proctor et al., (2010) Biomarkers in bladder cancer. Histopathology 57(1): 1-13.

Scholzen and Gerdes (2000) The Ki-67 protein: from the known and the unknown. J Cell Physiol 182(3): 311-322.

Pan et al., (2001) Study on liquid-based cytology for cervical carcinoma screening. Chinese Journal of Oncology 23(4): 309-321. Translated abstract.

Trunk et al., (2004) Morphologic characteristics of p16INK4a-positive cells in cervical cytology samples. Acta Cytol 48(6): 771-82.

METHODS AND COMPOSITIONS FOR IDENTIFYING A CELL PHENOTYPE

CROSS-REFERENCE TO RELATED APPLICATIONS

This application is a continuation-in-part of U.S. patent application Ser. No. 12/224,792, filed on Sep. 5, 2008, now U.S. Pat. No. 8,343,733 which is a 35 U.S.C. §371 National Phase Entry Application from PCT/IL2007/000281, filed on Mar. 6, 2007, and designating the United States, which claims the benefit of U.S. Provisional Application No. 60/778,839, filed on Mar. 6, 2006, the benefit of U.S. Provisional Application No. 60/778,944, filed on Mar. 6, 2006, the benefit of U.S. Provisional Application No. 60/778,900, filed on Mar. 6, 2006, and the benefit of U.S. Provisional Application No. 60/778,902, filed on Mar. 6, 2006.

The entire content of each earlier application is expressly incorporated herein by reference thereto.

FIELD OF THE INVENTION

The present invention is directed to a method of identifying cancerous or precancerous cells suspended in a liquid carrier, such as, a biological fluid.

BACKGROUND OF THE INVENTION

For decades, oncology research has focused on the search for detectable cancer specific markers, which can be used to verify the presence or absence of cancerous cells of various germlines in a tested biological specimen. Numerous cancer specific markers, including proteins, carbohydrates and nucleic acids, were found and characterized. However, none were shown to be pan-malignant, expressed by or secreted from all or even most cancer cell types. Hence, the quest is ongoing for a universal marker enabling effective oncodetection.

Normal and malignant cells have remarkably different phenotypes. The differences include the ability to form tumors in animal models, different differentiation state, ability to form colony in soft agar, lost of contact inhibition and spreading alterations, a faster metabolic rate and expression of tumor-specific markers.

The most common techniques utilized to detect cancerous cells are immunohistochemistry, immunocytochemistry and in situ hybridization. Those techniques are based on compounds of high affinity to a specific cellular molecule. These technologies are mostly used for phenotypic characterization of tumors (e.g., by implication of antibodies to intermediate filaments), detection of tumor markers of prognostic value (e.g., detection of p53 antigen), as well as the detection of other oncogenic expression features and nucleic acid sequences. Despite the high specificity of these techniques to detect malignancies, none of these techniques provides a pan-malignant tool for oncodiagnosis.

Other diagnostic cytology techniques include a narrow set of staining methods and compositions, some of which appeared many years ago, but are still being extensively used in present clinical cytology. This refers primarily to the alcohol-fixed Papanicolaou stain and the air-dried May-Grunwald-Giemsa (a version of which is known as Romanowsky) stain, while staining with hematoxylin and eosin, Shorr's staining for endocrine cytology and the Pappenheim method are more rarely used. However, those staining procedures are both time consuming and do not reveal any tinctorial selectivity for malignant cells.

It would be of utmost importance to discriminate between normal and malignant phenotype of cells in suspension, by a simple method, not limited to any particular cancer cell type. Particularly, there is an unmet need for differentiation techniques for detecting cancerous or precancerous cells suspended in biological fluids.

SUMMARY OF THE INVENTION

The present invention relates to methods for identifying the presence or absence of differentiated, undifferentiated, cancerous or precancerous cells of various germlines suspended in a liquid carrier, including, but not limited to, a biological specimen in a liquid form. The present invention is specifically useful for detecting the presence or absence of any cancer or metastases derived therefrom in a subject in need thereof. Utilizing the methods of the present invention cancerous or precancerous cells may be detected in biological fluids, such as, blood, thus allowing detection and monitoring of cancer via minimal invasive procedures. The method is based on a novel detection technology, capable of distinguishing between different cell phenotypes, by differential staining, at different metabolic or differentiation stages, without compromising the morphological evaluation. Advantageously, the method is highly sensitive and accurate allowing detection of even a single cancerous or precancerous cell in a given sample of cell suspension.

According to one aspect, the present invention provides a method of identifying at least one precancerous or cancerous cell present in a cell suspension, the method comprising: (a) providing a sample comprising a plurality of cells suspended in a liquid carrier; (b) fixing the plurality of cells onto a solid substrate; (c) contacting said plurality of cells with a Ficus plant extract; (d) contacting said plurality of cells with at least one dye; and (e) analyzing said plurality of cells, wherein when: (i) said at least one dye is an acidic dye a staining intensity of at least one cell above a predetermined threshold is indicative that said at least one cell is a differentiated cell; (ii) said at least one dye is a basic dye a staining intensity of at least one cell above a predetermined threshold is indicative that said at least one cell is an undifferentiated cell; (iii) said at least one dye comprises said acidic dye and said basic dye a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

According to another aspect, the present invention provides a method of diagnosing cancer in a subject in need thereof, the method comprising: (a) obtaining from said subject a sample comprising a plurality of cells suspended in a biological fluid; (b) fixing the plurality of cells onto a solid substrate; (c) contacting said plurality of cells with a Ficus plant extract; (d) contacting said plurality of cells with at least one dye; and (e) analyzing said plurality of cells, wherein when: (i) said at least one dye is an acidic dye a staining intensity of at least one cell above a predetermined threshold is indicative that said at least one cell is a differentiated cell; (ii) said at least one dye is a basic dye a staining intensity of at least one cell above a predetermined threshold is indicative that said at least one cell is an undifferentiated cell; (iii) said at least one dye comprises said acidic dye and said basic dye a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

According to one embodiment, contacting the plurality of cells with a Ficus plant extract is carried out after contacting the plurality of cells with at least one dye.

It should be noted that the order of steps (c) and (d) in the method of the invention is immaterial.

According to another embodiment, the at least one dye is a basic dye or an acidic dye. According to yet another embodiment, the basic dye is a fluorescent dye.

According to yet another embodiment, the basic dye is selected from the group consisting of Dahlia and new Fuchsin. Each possibility represents a separate embodiment of the present invention.

According to yet another embodiment, the acidic dye is Fast Green. According to yet another embodiment, the acidic dye is Light Green. According to yet another embodiment, the at least one dye is a single dye. According to yet another embodiment, the at least one dye comprises two dyes.

According to yet another embodiment, the Ficus plant is Ficus elastica. According to yet another embodiment, the Ficus plant is from the subgenus Urostigma. According to yet another embodiment, the Ficus plant extract is obtained from a leaf tissue. According to yet another embodiment, the Ficus plant extract comprises a crude plant extract. According to yet another embodiment, the Ficus plant extract is an ethanol extract of a leaf tissue. According to yet another embodiment, the ethanol extract comprises 70% ethanol. According to yet another embodiment, the Ficus plant extract is supplemented with positively charged ions. According to yet another embodiment, the positively charged ions are selected from the group consisting of magnesium and calcium. Each possibility represents a separate embodiment of the present invention.

According to yet another embodiment, the analyzing is performed using an optic microscope.

According to yet another embodiment, the sample comprises a biological fluid comprising a plurality of cells. According to yet another embodiment, the biological fluid is selected from the group consisting of blood, urine, saliva, cerebrospinal fluids, ascitic fluid and semen. Each possibility represents a separate embodiment of the present invention.

According to yet another embodiment, the liquid carrier is a biological fluid.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to methods of detection a premalignant and/or a malignant cellular phenotype in a liquid biological specimen. The methods are based on a unique cellular staining approach. The present invention successfully addresses the shortcomings of the presently known configurations by providing methods which can be used to distinguish between various types of cancerous or precancerous cells to normal cells, with especially high sensitivity. Specifically, the present invention can be used to diagnose cancer, or metastases derived therefrom in biological liquid samples obtained from a subject in need thereof.

The cellular staining procedure of the invention is based on the differential staining obtained by contacting cells with a plant extract of Ficus in combination with one or more dyes. Said dyes, specifically, acidic and/or basic dyes facilitate the unique cellular staining methodology of the invention.

Without being bound by any theory or mechanism, normally differentiated cells have higher affinity to acidic dyes than less differentiated cells (e.g., metabolically impaired or malignant). Likewise those less differentiated cells exhibit higher affinity to basic dyes than normally differentiated cells. The present staining technique accentuates these differences in staining (i.e., differential staining). The result is a binary chromogenic response, with rapid metabolizing cells such as malignant or non-differentiated cells, staining red/purple, and normal or highly differentiated cells with a slower metabolism, staining green or bluish green. Most importantly, this differential staining is achieved without compromising the acuity of visualization of the morphological differences of cell substructures detectable under the microscope using conventional staining methods, thus allowing also traditional morphological based analysis of the stained cells.

Furthermore, the method of the invention provides differential staining with high sensitivity and specificity, thereby the method may be applied on sample having only a few cancer cells diluted among non cancer cells.

According to one aspect, the present invention provides a method of identifying at least one precancerous or cancerous cell present in a cell suspension, the method comprising: (a) providing a sample comprising a plurality of cells suspended in a liquid carrier; (b) fixing the plurality of cells onto a solid substrate; (c) contacting said plurality of cells with a Ficus plant extract; (d) contacting said plurality of cells with at least one dye; and (e) analyzing said plurality of cells, wherein when: (i) said at least one dye is an acidic dye a staining intensity of at least one cell above a predetermined threshold is indicative that said at least one cell is a differentiated cell; (ii) said at least one dye is a basic dye a staining intensity of at least one cell above a predetermined threshold is indicative that said at least one cell is an undifferentiated cell; (iii) said at least one dye comprises said acidic dye and said basic dye a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

According to one embodiment, contacting the plurality of cells with a Ficus plant extract is carried out thereafter contacting the plurality of cells with at least one dye. According to yet another embodiment, the staining steps may be carried out in any order.

As used herein the phrase "cell suspension" refers to cells in a liquid carrier. According to one embodiment, the liquid carrier is a biological fluid. The biological fluid may be any bodily fluid including, but not limited to, blood, plasma, saliva, semen, urine, cerebrospinal fluid, milk, pleural fluid, lymph fluid, peritoneal fluid, vaginal secretions, sweat, ascetic fluid and combinations thereof. Cell suspension of the present invention may be cellular samples obtained from biopsies (surgical biopsies, fine needle aspirates, oral swab and the like). Methods of biopsy retrieval are well known in the art and much depend on the kind of cancer or any other medical condition to be detected. Typically, biological samples (e.g., cell smear or fluids obtained by fine needle aspiration) comprise heterogeneous populations of cells. Such heterogeneous populations may comprise heterogeneously differentiated cells. For example the population of cells may comprise malignant or pre-malignant cells as well as normal healthy cells. Alternatively, such a population of cells may comprise metabolically normal and metabolically impaired cells. Additionally or alternatively, the population may comprise fetal and/or embryonic cells as well as maternal cells. Thus, the present invention is useful in distinguishing between such heterogeneous populations of cells based on the different differentiation and/or metabolic state of the cells.

The terms "liquid sample" and "liquid specimen" are interchangeable and encompasses a liquid carrier comprising cells suspended therein. According to one embodiment liquid specimen comprises semi liquid specimen. The "sample" or "specimen" may be obtained from any liquid or semi liquid tissue or tissue comprising liquids to form a specimen suitable for staining according to the methods of the invention.

According to one embodiment, the method of the invention is applied on a sample comprising a biological fluid comprising cells, wherein the sample is selected from the group consisting of a blood sample, a urine sample, a saliva sample, a cerebrospinal sample, an effluent (e.g. lung effluent), an ascitic fluid sample and a semen sample and the alike. Each possibility represents a separate embodiment of the present invention.

According to another embodiment, the biological sample or cell suspension derived therefrom may be treated prior to being subjected to the steps of the methods of the invention. The sample may be pretreated to remove unwanted cells using methods well known in the art (e.g. size exclusion, selective cell lysis etc.). For example, red blood cells of a blood sample can be selectively lysed using well known osmotic lysing techniques, while other cell fractions of blood can be selectively removed using well known blood fractionation approaches.

The sample may be pretreated to enrich the subpopulation of desirable cells using methods well known in the art, such as, size exclusion and selective antibody binding, among other methods. For example, malignant cells can be selectively attached to a solid phase via specific markers, and then isolated from the rest of the cells, e.g., white blood cells, in the sample. Alternatively, the white blood cells in the sample can be depleted using fractionation procedures, thereby maintaining in the sample only the desired cancer cells.

According to yet another embodiment, the "sample" or "specimen" may be diluted or concentrated prior to being subjected to the steps of the method of the invention.

According to yet another embodiment, the solid substrate is a microscope slide. A variety of solid substrates are suitable for applying the sample for staining according to the method of the invention. The substrate may comprise glass or plastic, but suitable substrates may also include a polymer material, a ceramic material or a superconducting material.

According to yet another embodiment, the methods of the present invention comprise the step of fixing the cells. According to one embodiment, fixing or fixating of cells relates to a process by which biological tissues are preserved from decay, thereby preventing autolysis or putrefaction. Typically, fixation terminates any ongoing biochemical reactions, and may also increase the mechanical strength or stability of the treated cells. Fixing of cells may be performed according to any fixing procedure known in the art including, but not limited to, chemical fixation, freeze fixation, air-fixing and the alike. Chemical fixation refers to fixation with a chemical reagent. Suitable chemical reagents include, but are not limited to, formaldehyde, gluteraldehyde, methanol, ethanol, acetic acid, and the alike. According to some embodiments, cells are fixated with trichloroacetic acid (TCA). According to other embodiments, fixation with a chemical reagent may be carried out for predetermined time course. For example fixation may be carried out for a time period within the range of 10 minutes to 2 hours. According to further embodiments, fixation with TCA is carried out for a time period of one hour.

According to one embodiment, the methods of the present invention comprise a step of contacting the cells with a Ficus plant extract. According to another embodiment, the methods of the present invention further comprise a step of contacting the cells with at least one dye.

As used herein the term "contacting" refers to "subjecting", "incubating" or "exposing" the cells to Ficus plant extract or to a dye, to facilitate staining and thereby detection of the cells via staining. The cells may be contacted, incubated or exposed to the Ficus plant extract, or to one or more dyes, for a time period which enables detection of precancerous or cancerous cells such that they will be detectable via one of the detection approaches described herein. For example, suitable incubation periods of the sample with an extract of Ficus, include about 1-20 minute, about 1-10 minutes, about 1-5 minutes, about 2-10 minutes, about 2-6 minutes, or about 2-4 minutes. In general, incubation time with the additional dye is shorter, and is within the range of 10 sec. to 1 minute.

As used herein, "Ficus plant extract" refers to an extract obtained from Ficus plant. According to one embodiment, the Ficus plant extract is derived from the subgenus Urostigma. According to another embodiment, the Ficus plant extract is derived from Ficus elastica species. The extract may be prepared from various portions of the plant such as form the leaves. According to yet another embodiment, the Ficus plant extract is an ethanol extract. The ethanol extract of the plant tissue may comprise about 10% (v/v ethanol in water), about 20%, about 30%, about 40%, about 50% ethanol, about 60% ethanol, about 70% ethanol, about 80% ethanol about 90% ethanol or about 100% ethanol. Measures should be taken however not to over dilute the extract, as this may affect the subsequent staining. Leaves are obtained from Ficus elastica. Any size or weight of leaves is suitable for this purpose, including, but not limited to, between 15 and 25 grams in weight and between 18 and 30 centimeter in length (measured from the base of the leaf to the tip). Typically, extracts are obtained from a 1,000 gram sample of leaves cut into 1-2 cm slices which are then mixed with 3 liter of 70% ethanol (EtOH) and kept for 14 days (room temperature) in a sealed container. Thereafter, the liquid is separated from the solids and kept for further use in room temperature. The liquid extract may be allowed to age in the container for at least 10 days and up to one month, at room temperature.

Alternatively, the leaf slices may be dried to a water content of about 4% (for example, at 65° C. for 24 hours) and the dry leaf material is blended into a powder (700-1,000 micron). The powder is subjected to extraction in a reflux system. Extraction may be carried out for 1 hour in 70% ethanol, at 40° C. Three sequential extractions may be performed, each time the powder is re-extracted. Quantity of 70% ethanol in each extraction may be as follows: first—1:5; second—1:4; third—1:3. The three resulting extracts may be mixed and filtered (e.g. in vacuum filter, paper No. 40). The mixed, filtered extract may be evaporated until a steady weight is obtained. Evaporation may be carried out in a rotor evaporator under vacuum at 60° C. Typically, the resulting powder has a water content of 3%. The powder may be blended further in a grinder. The powder extract can be reconstituted for use as a conditioning reagent. Reconstitution may be carried out by suspending the powder in 70% ethanol with 1.3% total dissolved solids (TDS) w/v and a final pH of 7.4.

To accentuate the difference between cells of different metabolic or differentiation states, the cells are contacted with Ficus plant extract in combination with at least one dye. According to one embodiment, the methods of the present invention comprise the step of contacting the cells with a dye prior to or following contacting said cells with a Ficus plant extract. According to yet another embodiment, the at least one dye is a single dye. According to yet another embodiment, the at least one dye comprises two dyes. According to one embodiment, the steps of contacting the cells with a dye and a Ficus plant extract are effected sequentially.

As used herein, the term "dye" refers to any substance that imparts color to a biological tissue, cells, cellular compartments or molecules comprising the cells. The dyes which have been found to be of immediate utility for the purpose of implementing the present invention are disclosed herein, although other dyes not herein described may be useful as well for this purpose. Thus, although the description of the present invention provides dyes which manifest color in the visible range of the spectrum, it may easily be envisioned that, through the use of appropriate filters, illuminations, configurations, or means for detection, dyes which are invisible to direct observation may prove equivalent to the visible dyes described herein for implementing the present invention.

According to one embodiment, the at least one dye is a basic dye. Examples of basic dyes that can be used with the present approach include, but are not limited to, Victoria Pure Blue, Basic Brown G, Malachite Green Crystals, Chrysoidine, Methyl Violet, Magenta Crystals, Auramine O, Rhodamine, Acriflavine, Acridine orange, Coriphosphine O, Acridine yellow, Phosphine E, Thioflavine T, Berberine sulfate, Atebrine and Rivanol. Of these Rhodamine, Auramine O, Acriflavine, Acridine orange, Coriphosphine O, Acridine yellow, Phosphine E, Thioflavine T, Berberine sulfate, Atebrine and Rivanol are preferred for their unique fluorescence signature.

According to one embodiment, the basic dye is a fluorescent dye. According to yet another embodiment, the basic dye is selected from the group consisting of Dahlia and new Fuchsin. Each possibility represents a separate embodiment of the present invention. According to yet another embodiment, the dye is New Fuchsin.

New Fuchsin stains cancerous or precancerous cells preconditioned or post-conditioned as described herein, with an intense red color, while leaving normal cell stained with a lighter less intense tone of red (light red or pink). Typically, this concentrates at the nucleus and cytoplasm and is indicative of cancerous or precancerous phenotype. New Fuchsin is available as powder from various manufacturers such as Sigma (Cat. No. N0638), Fluka (Cat. No. 72200) or Merck (Cat. No. 1052260100). New Fuchsin may be used at a concentration of about 0.1%-1% (w/v). A New Fuchsin solution may be water-based and/or ethanol-based and may include about 2%-40% ethanol. According to one embodiment, the concentration of New Fuchsin is about 0.25% in 20% EtOH.

According to another embodiment, the at least one dye is an acidic dye. According to yet another embodiment, the acidic dye is Fast Green. According to yet another embodiment, the acidic dye is Light Green.

According to yet another embodiment, cells stained according to the staining procedure of the invention may be analyzed using microscopic detection methods known in the art. Stained cells may be analyzed using an optic microscope. In cases where analysis is effected via microscopic examination (either by a pathologists or an automated image analysis system), the basic dye can be any dye that is optically detectable.

According to yet another embodiment, the methods of the present invention may further comprise a step performing morphological analysis aimed to detect malignancy-related cellular morphologic alterations, including, but not limited to, increased nucleus-cytoplasm ratio, irregularities of chromatin and nuclear contour, among others.

Additional staining modalities or analyses can be carried out in combination with the methods of the present invention. However, it is to be understood, that the staining methods of present invention do not compromise cell morphology.

According to yet another embodiment, additional staining modalities for morphological analyses are carried out by staining the cells with at least one dye. According to yet another embodiment, the dye is a basic dye. According to yet another embodiment, the dye is a triamnotriphenylmethane derivative. According to yet another embodiment, the dye is a diazo derivative. According to yet another embodiment, the dye is any combination of one or more acidic dye, basic dye, triaminotriphenylmethane derivatives and diazo derivatives. Each possibility represents a separate embodiment of the present invention.

According to yet another embodiment, the dye is selected from the group consisting of Hematoxylin Gill, Azure, A, Giemsa, Yellow, Phloxine, Light Green, Fast Green, New Fuchsin, Dahlia, Basic Fuchsin, Methyl Violet, Gentian Violet, Methyl Violet 6b, Crystal Violet, Pararosanilin, Rosanilin, Magenta I, Isorubin, Fuchsin NB, FIAT-764, Spiller's Purple, Bismark Brown R, Bismark Brown Y, Bismark Brown Eosine Conjugate, Bismark Brown Phloxine Conjugate, Phoenix Brown A, or any combinations thereof. Each possibility represents a separate embodiment of the present invention.

According to one embodiment, the dye is a red dye. As used herein, the term "red" refers not only to the color red but as well to related shades and hues such as violet, pink or pinkish, purple or purplish, or magenta. According to yet another embodiment, the red dye is New Fuchsin. The concentration of the dye will be determined empirically based on the need of the assay. A suitable concentration of a dye is one that enables the detection of the staining of the cell with the dye, using any of the detection methods as described herein.

As used herein the phrase "staining above a predetermined intensity" refers to at least 10%, 20%, 30%, 40%, 50%, 80%, 100% (i.e., two-fold), 3 fold, 5 fold or 10 fold or higher staining intensity as compared to a reference cell. The reference cell may be a normally differentiated cell, preferably obtained from a similar specimen or organ as the tested cell suspicious of an undifferentiated phenotype. To better improve the visual distinguish between cells of different differentiation or metabolic states, two different dyes are used in sequence (e.g., an acidic dye and a basic dye). Thus, for example, the cells may be first stained with a basic dye (e.g., red) and subsequently with an acidic dye (e.g., green). In line with the teachings of the invention, normally differentiated cells are stained green (or not at all) while less differentiated cells will be stained red. Other dyes are further described hereinbelow.

According to another aspect, the present invention provides a method of diagnosing cancer in a subject in need thereof, the method comprising: (a) obtaining from said subject a sample comprising a plurality of cells suspended in a biological fluid; (b) fixing the plurality of cells onto a solid substrate; (c) contacting said plurality of cells with a Ficus plant extract; (d) contacting said plurality of cells with at least one dye; and (e) analyzing said plurality of cells, wherein when: (i) said at least one dye is an acidic dye a staining intensity of at least one cell above a predetermined threshold is indicative that said at least one cell is a differentiated cell; (ii) said at least one dye is a basic dye a staining intensity of at least one cell above a predetermined threshold is indicative that said at least one cell is an undifferentiated cell; (iii) said at least one dye comprises said acidic dye and said basic dye a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

As used herein the phrase "subject in need thereof includes, but is not limited to, an animal or human subject who is at risk of having cancer (e.g., a genetically predisposed subject, a subject with medical and/or family history of cancer, a subject who has been exposed to carcinogens, occupational hazard, environmental hazard) and/or a subject who exhibits suspicious clinical signs of cancer (e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Additionally or alternatively, the subject in need thereof may be a healthy human subject undergoing a routine well-being check up. Analyzing the presence of malignant or pre-malignant cells may be effected by retrieving a biological sample (e.g., fluids from a sample of fine needle aspiration or a blood sample) from the subject.

The biological samples may be obtained through a third party, such as a party not performing the analysis. For example, the sample may be obtained through a clinician, physician, or other health care manager of a subject from which the sample is derived.

The volume of the biological sample used for analyzing based on the method of the invention may be in the range of between 0.1-250 mL, or less than about 250 mL, such as, 15, 10, 9, 8, 7, 6, 5, 4, 3, 2, 1 or 0.1 mL.

As used herein, the term "cancer" is used interchangeably with the terms malignancy, malignant or neoplasm, and refers to a disease of cells characterized by an abnormal growth of cells which tend to proliferate in an uncontrolled manner and, in some cases, to metastasize.

A "cancer cell" or a "malignant cell" as used herein, is a cell which has been released from normal cell division control, is thus characterized by an abnormal growth and a tendency to proliferate in an uncontrolled way and, in some cases, to metastasize. The definition of a malignant cell comprise, but is not limited to, a neoplastic cell, a pre-malignant cell, a metastatic cell, a malignant cell, a tumor cell, an oncogenic cell, a cell with a cancer genotype, a cell of malignant phenotype, a cell with a malignant genotype, an oncogene transfected cell, a virus transformed cell, a cell which expresses a marker for an oncogene, a cell which expresses a marker for cancer, or a combination thereof.

As used herein the terms "precancerous" and "pre-malignant" are interchangeable and relate to cellular transformation that may, but do not always, become malignant, cancerous.

A "non-malignant cell", as used herein, refers to a normal cell, characterized by a normal growth.

Due to its broad applicability, the present approach can be used to identify precancerous or cancerous cells (and thus diagnose cancer) of a broad range of cell types and pathologies. Examples of cancerous or precancerous cells that can be identified using the present approach include, but are not limited to an adenocarcinoma cell, an adrenal gland tumor cell, an ameloblastoma cell, an anaplastic cell, anaplastic carcinoma of the thyroid cell, an angiofibroma cell, an angioma cell, an angiosarcoma cell, an apudoma cell, an argentaffmoma cell, an arrhenoblastoma cell, an ascites tumor cell, an ascitic tumor cell, an astroblastoma cell, an astrocytoma cell, an ataxia-telangiectasia cell, an atrial myxoma cell, a basal cell carcinoma cell, a bone cancer cell, a bone tumor cell, a brainstem glioma cell, a brain tumor cell, a breast cancer cell, a Burkitt's lymphoma cell, a cancerous cell, a carcinoid cell, a carcinoma cell. It should be understood, that the present invention relates to methods for staining cells obtained from various biological liquid samples, such as, blood and saliva among others. Thus, a blood sample may contain cancer cells that are not necessarily cells from the primary tumor but are rather metastatic cells.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1

Identification of Human Breast Cancer Cells in a Heterogeneous Cell Suspension

Figure 1A:
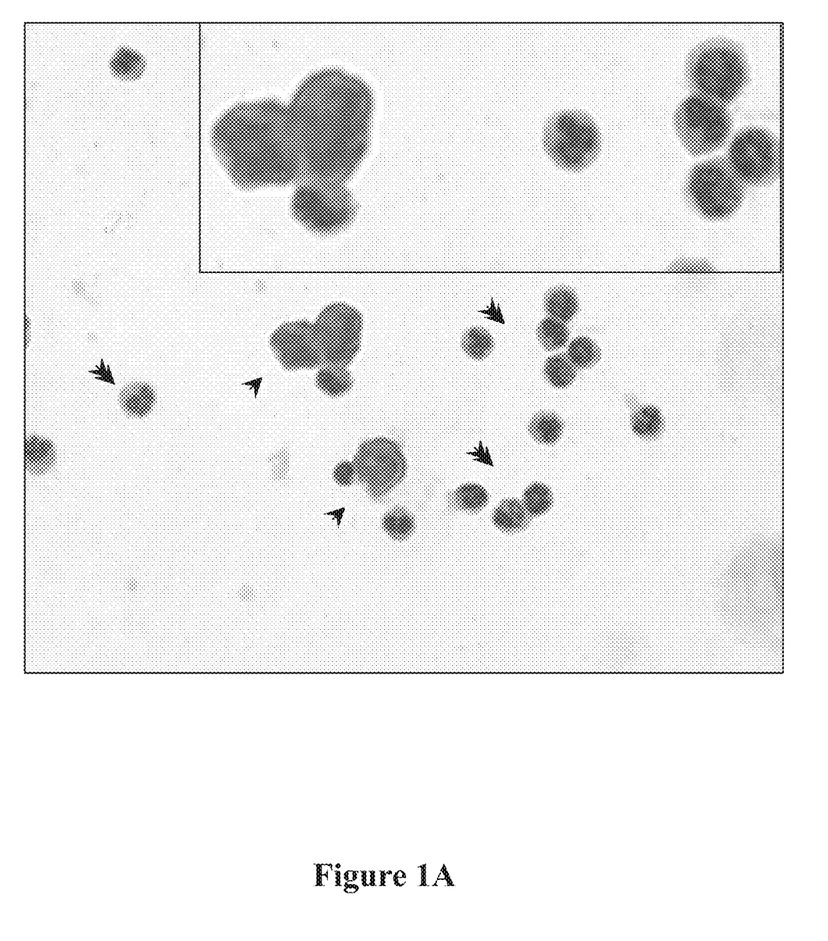
FIG. 1A is a photomicrograph of a sample of cultured breast cancer cells among white blood cells (WBCs) stained according to the methods of the invention.
Figure 1B:
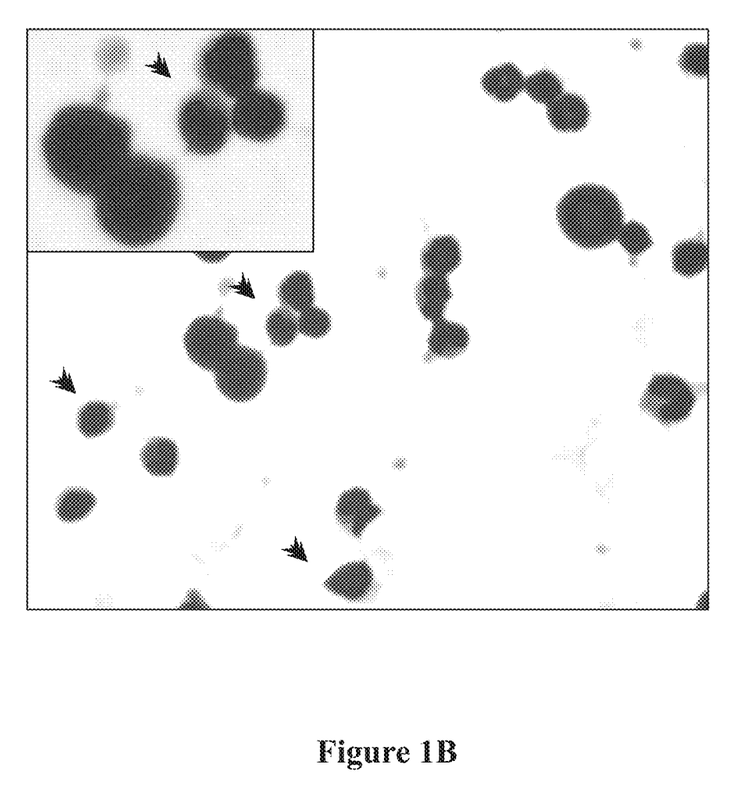
FIG. 1B is a photomicrograph of cultured breast cancer cells among white WBCs stained with Giemsa.

Cancer cells spiked into smears of white blood cells (WBCs) were used as a model for demonstrating the staining procedure of the invention. Cells ($2\times10^4$) from the human breast carcinoma/adenocarcinoma cell lines (BT474, MDA-MB468, MCF-7, or BT549) were spiked in PBS containing $2\times10^6$ WBC fraction after erythrocyte depletion. 100 µl drops were dried on Superfrost slides. Staining procedures were affected in a slide container at room temperature. Slides were then washed using running deionized water (DIW) for 10 seconds. Cells were then fixed in 20% Tricloroacetic acid (TCA) for 1 hour and washed. For counter staining, slides were incubated for 1 minute in Gill's hematoxylin, washed in running tap water until the water was clear, and then the slides were washed for 10 seconds in running DIW. Slides were incubated in Ficus extract solution for 2 minutes, washed, then incubated in New Fuchsin for 1 minutes (0.25% in ethanol 20%), washed, then incubated in Alcian Blue for 3.5 minutes (0.5% DIW), washed and dipped 3 times in Fast Green (2% in ethanol 20%). Thereafter slides were washed, dried under a fume hood, soaked for 10 seconds in Xylene and mounted in Entellan. Slides were viewed under the microscope for detecting stained cells. As can be seen in FIG. 1A, cancer cells were stained in red/purple (arrowheads; darker shades of gray) whereas WBCs are stained in blue/green (double arrowheads; lighter shades of gray). Moreover, the morphology of all cell types, namely of cancer cells as well as of WBCs was preserved, allowing further confirmation of staining analysis. For comparison, FIG. 1B demonstrates a similar cell smear stained with the commonly-used Giemsa stain for WBC, in which cancer cells (arrowheads) are hardly distinguishable from WBC (double arrowheads). Stated otherwise, using the common Giemsa stain, all cells are non-differentially stained the same. Three other breast cancer cell lines gave similar and reproducible results. For quantitative evaluation, morphologically identified cells were scored according to cytoplasm color. Results of four independent experiments (spiking of MDA-MB468, MCF-7, or BT549 cells into WBCs) clearly show a very high level of accuracy between color and morphology analysis and cell identification presenting about 99.5% 90-95% of the WBCs and the cancer cells, respectively, being diagnosed correctly. Table 1 exemplifies the performance of the BT-474 cell line.

TABLE 1

Performance evaluation in BT-474 cells spiked in WBCs.

| Item | Number/statistics |
|---|---|
| No. of fields counted | 26 |
| No. of cancer cells | 373 |
| No. of WBCs | 5178 |
| *Miss correlation between WBCs and color in % | 0.6% |
| *Miss correlation between cancer cells and color in % | 3.5% |
| Specificity | 99.4% ± 0.3% |
| Sensitivity | 93.5% ± 2.5% |

*Miss correlation refers to the error in the specificity and sensitivity of the stating. This is calculated based on the lack of correlation between the morphology and the staining procedure of the invention.

Taken together, the results clearly demonstrate that the staining technology of the invention is proficient in detecting rare cancer cells in a sample.

Example 2

Analysis of Cells in a Blood Sample

About 10 mL of peripheral blood sample is obtained from a subject. Sample can be further processed as is, or undergo either enrichment of tumor cells or depletion of normal cells. Cell population is concentrated using a separator. After separation, fluid is aspirated and discarded and the remaining cells are fixed onto a microscope slide.

For counter staining, slides are incubated for 1 minute in Gill's hematoxylin, washed in running tap water until the water is clear, and then the slides are washed for 10 seconds in running DIW. Slides are incubated in Ficus extract solution for 2 minutes, washed, then incubated in New Fuchsin for 1 minutes (0.25% in ethanol 20%), washed, then incubated in Alcian Blue for 3.5 minutes (0.5% DIW), washed and dipped 3× in Fast Green (2% in ethanol 20%). Thereafter slides are washed, dried under a fume hood, soaked for 10 seconds in Xylene and mounted in Entellan. Slides are viewed under the microscope for detecting stained cells.

Example 3

Analysis of Cells in a Pleural Effusion

One liter of a pleural effusion is obtained from a patient. The fluid is centrifuged, the cells resuspended in a small volume of liquid carrier to obtain a concentrated cell sample. After resuspension, the cells are fixed onto a microscope slide.

For counter staining, slides are incubated for 1 minute in Gill's hematoxylin, washed in running tap water until the water is clear, and then the slides are washed for 10 seconds in running DIW. Slides are incubated in Ficus extract solution for 2 minutes, washed, then incubated in New Fuchsin for 1 minutes (0.25% in ethanol 20%), washed, then incubated in Alcian Blue for 3.5 minutes (0.5% DIW), washed and dipped 3× in Fast Green (2% in ethanol 20%). Thereafter slides are washed, dried under a fume hood, soaked for 10 seconds in Xylene and mounted in Entellan. Slides are viewed under the microscope for detecting stained cells.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of identifying at least one precancerous or cancerous cell present in a cell suspension, the method comprising:
 (a) providing a sample comprising a plurality of cells suspended in a liquid carrier;
 (b) fixing the plurality of cells onto a solid substrate;
 (c) contacting said plurality of cells with a Ficus plant extract;
 (d) contacting said plurality of cells with at least one dye; and
 (e) analyzing said plurality of cells,
 wherein when: (i) said at least one dye is an acidic dye, a staining intensity of at least one cell above a predetermined threshold is indicative that said at least one cell is a differentiated cell; (ii) said at least one dye is a basic dye, a staining intensity of at least one cell above a predetermined threshold is indicative that said at least one cell is an undifferentiated cell; (iii) said at least one dye comprises said acidic dye and said basic dye, a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

2. The method of claim 1, wherein said at least one dye is a basic dye or an acidic dye.

3. The method of claim 2, wherein said basic dye is selected from the group consisting of Dahlia and new Fuchsin.

4. The method of claim 2, wherein said acidic dye is selected from the group consisting of Fast Green and Light Green.

5. The method of claim 1, wherein said at least one dye is a single dye or comprises two dyes.

6. The method of claim 1, wherein said Ficus plant is Ficus elastica.

7. The method of claim 1, wherein said Ficus plant extract is an ethanol extract of a leaf tissue.

8. The method of claim 1, wherein contacting said plurality of cells with a Ficus plant extract is carried out after contacting said plurality of cells with at least one dye.

9. The method of claim 1, wherein said sample is selected from the group consisting of a blood sample, a urine sample, a saliva sample, a cerebrospinal sample, an ascitic fluid sample and a semen sample.

10. The method of claim 1, wherein said liquid carrier is a biological fluid selected from the group consisting of: blood, plasma, saliva, semen, urine, cerebrospinal fluid, ascetic fluid and combinations thereof.

11. The method of claim 1, wherein said at least one undifferentiated cell is a malignant or pre-malignant cell.

12. A method of diagnosing cancer in a subject in need thereof, the method comprising:
   (a) obtaining from said subject a sample comprising a plurality of cells suspended in a biological fluid;
   (b) fixing the plurality of cells onto a solid substrate;
   (c) contacting said plurality of cells with a Ficus plant extract;
   (d) contacting said plurality of cells with at least one dye; and
   (e) analyzing said plurality of cells,
   wherein when: (i) said at least one dye is an acidic dye a staining intensity of at least one cell above a predetermined threshold is indicative that said at least one cell is a differentiated cell; (ii) said at least one dye is a basic dye a staining intensity of at least one cell above a predetermined threshold is indicative that said at least one cell is an undifferentiated cell; (iii) said at least one dye comprises said acidic dye and said basic dye a staining intensity of at least one cell above a predetermined threshold with said acidic dye is indicative that said at least one cell is a differentiated cell and a staining intensity of at least one cell above a predetermined threshold with said basic dye is indicative that said at least one cell is an undifferentiated cell.

13. The method of claim 12, wherein said at least one dye is a basic dye, or an acidic dye.

14. The method of claim 13, wherein said basic dye is selected from the group consisting of Dahlia and new Fuchsin.

15. The method of claim 13, wherein said acidic dye is selected from the group consisting of Fast Green and Light Green.

16. The method of claim 12, wherein said at least one dye is a single dye or comprises two dyes.

17. The method of claim 12, wherein said Ficus plant is Ficus elastica.

18. The method of claim 12, wherein said Ficus plant extract is an ethanol extract of a leaf tissue extract.

19. The method of claim 12, wherein said sample is selected from the group consisting of a blood sample, a urine sample, a saliva sample, a cerebrospinal sample, an ascitic fluid sample and semen sample.

20. The method of claim 12, wherein said at least one undifferentiated cell is a malignant or pre-malignant cell.

* * * * *